United States Patent [19]

Rogier

[11] 4,307,224
[45] Dec. 22, 1981

[54] POLYMERIC POLYOLS

[75] Inventor: Edgar R. Rogier, Minnetonka, Minn.

[73] Assignee: Henkel Corporation, Minneapolis, Minn.

[21] Appl. No.: 123,089

[22] Filed: Feb. 20, 1980

Related U.S. Application Data

[63] Continuation-in-part of Ser. No. 26,854, Apr. 4, 1979, abandoned, and a continuation-in-part of Ser. No. 81,953, Oct. 4, 1979, which is a continuation of Ser. No. 26,858, Apr. 4, 1979, Pat. No. 4,216,343.

[51] Int. Cl.$^3$ ............................................. C08G 63/12
[52] U.S. Cl. .................................. 528/272; 528/296; 528/308; 528/309
[58] Field of Search ............... 528/272, 296, 308, 309

[56] References Cited

U.S. PATENT DOCUMENTS

| | | | |
|---|---|---|---|
| 3,290,387 | 12/1966 | Bernandy et al. | 568/854 |
| 3,433,751 | 3/1969 | Yotsuzuka et al. | 521/914 |
| 4,110,268 | 8/1978 | Longley et al. | 521/174 |
| 4,124,570 | 11/1978 | Scheibelhoffer et al. | 528/296 |
| 4,216,343 | 8/1980 | Rogier | 528/85 |

*Primary Examiner*—Maurice J. Welsh
*Attorney, Agent, or Firm*—Gordon W. Hueschen

[57] ABSTRACT

This invention relates to polymeric polyols based on bis(hydroxymethyl)octadecanol with polybasic acids to make polyester polyols which have acid numbers less than about ten, and which polyester polyols are useful for a variety of known polyol applications as well as for making new urethane polymers which are advantageously useful in coatings, elastomers, adhesives, and caulking and sealing compositions or formulations.

7 Claims, No Drawings

POLYMERIC POLYOLS

CROSS REFERENCE TO RELATED APPLICATIONS

This application is a continuation-in-part of my application Ser. No. 26,854, filed Apr. 4, 1979, now abandoned. This application is also a continuation-in-part of application Ser. No. 81,953, filed Oct. 4, 1979, which application is a continuation of application Ser. No. 26,858, filed Apr. 4, 1979 now U.S. Pat. No. 4,216,343, issued Aug. 5, 1980.

FIELD OF INVENTION AND PRIOR ART

This invention relates to polymeric polyols. More particularly, this invention relates to polymeric polyols based on bis(hydroxymethyl)octadecanol with polybasic acids to make polyester polyols which have low acid numbers, e.g., less than one, and which polyester polyols are useful for a variety of known polyol applications as well as for making new urethane polymers which are advantageously useful in coatings, elastomers, adhesives, and caulking and sealing compositions or formulations.

In U.S. application Ser. No. 81,953, filed Oct. 4, 1979, there are described and claimed some gem-bis(hydroxymethyl) alcohol compounds having the general formula

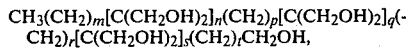

wherein n, plus q, and s are separate numbers totaling 1 to 3; each of n, q, and s is 0 or 1; the sum of m through t totals 12 to 20; and, t is 3 or greater. The preferred specific alcohols of that formula are gem-bis(hydroxymethyl) octadecanols. Also described therein are a short history of hydroformylation technology for making alcohols, a list of prior patents relating to hydroformylation products, and methods for preparing the specific new polybis(hydroxymethyl) alkanols claimed therein.

Hydroformylation is basically defined as the addition of a formyl group through the reaction of an unsaturated compound with carbon monoxide and hydrogen. The basic technology for the manufacture of hydroformylated products and, consequently, their derivatives is amply set out hereinafter. Among the difficulties which must be met in the manufacture of hydroformylated products is the consideration that hydrogen gas, an explosive, and carbon monoxide, a hazardous material, are utilized in the process. Hydroformylation processes are also dependent on expensive metallic catalysts, such as carbonyls, which have high toxicity and high cost. The conditions for running a hydroformylation reaction also involve the use of substantial temperature and pressure, thus necessitating costly equipment which must be maintained.

Thus, due to the various factors and considerations which go into the manufacture of hydroformylated products and their derivatives, it is essential that the reactions, individually and cumulatively, give high purity of the desired end product and high yield, thereby avoiding excessive handling of hazardous materials while minimizing the high capital cost and maintenance of such production facilities.

In the past, several attempts have been made to prepare hydroformylated products or similar materials, such as is described in U.S. Pat. No. 2,437,600 to Gresham et al., issued Mar. 9, 1948. The Gresham patent relates to the synthesis of organic oxygen containing compounds, in particular, aldehydes. U.S. Pat. No. 2,533,276 to McKeever et al., issued Dec. 12, 1950, describes ester-acetals obtained with cobalt catalysts. U.S. Pat. No. 2,599,468 to McKeever, issued June 3, 1952, describes the process of preparing nonadecyl glycols.

U.S. Pat. No. 3,040,090, issued June 19, 1962, to Alderson et al., discusses the reaction of hydrocarbons with aldehydes and higher alcohols in methanol to prepare organic oxy compounds. The Alderson et al. patent sets forth a number of metallic catalysts which may be employed in effecting the reactions described therein.

In U.S. Pat. No. 3,043,871, issued July 10, 1962, to Buchner et al., the production of heptadecane-dicarboxylic acid is described. Foreman et al., in U.S. Pat. No. 3,227,640, issued Jan. 4, 1966, describes the production of olefinically-unsaturated alcohols which are of use in manufacturing some of the end products of the present invention. U.S. Pat. No. 3,420,898, issued to Van Winkle et al., on Jan. 7, 1969, discusses the use of cobalt complexes with certain phosphine compounds in the production of primary alcohols with carbon monoxide and hydrogen.

U.S. Pat. No. 3,530,190, issued Sept. 22, 1970, to Olivier, discusses hydrocarbonylation of olefins using certain metal salts. The foregoing reference also discusses the recovery of the complexed metal catalyst. In a patent to Ramsden, issued Jan 16, 1973 as U.S. Pat. No. 3,711,560, the production of polyolefins and other oxygenated organic compounds which are polyunsaturated is discussed.

In U.S. Pat. No. 3,787,459, issued Jan. 22, 1974, to Frankel, a process is described for converting unsaturated vegetable oil into formyl products which are subsequently reduced to the corresponding hydroxymethyl derivative or oxidized to the corresponding carboxy products. U.S. Pat. No. 3,899,442, issued Aug. 12, 1975, to Friedrich, discusses a complementary system to that of the Frankel patent, whereby rhodium catalysts are recovered from the spent hydroformylation reactants. Frankel, again in the U.S. Pat. No. 3,928,231, issued Dec. 23, 1975, discusses a process of preparing carboxy acid products in high yields while minimizing isomerization of the starting unsaturated vegetable oil. Miller et al., in U.S. Pat. No. 4,093,637, issued June 6, 1978, discusses the use of formyl stearic acid to prepare bis acyloxymethylstearic acid which is stated to be useful as a plasticizer.

U.S. Pat. No. 3,931,332, issued Jan. 6, 1976, to Wilkes, discusses hydroformylation reactions in which the destructive disassociation of the catalyst is inhibited by the presence of organic nitrogen compounds. Reichspatentamt Patentschrift No. 745,265, to Mannes et al., published Mar. 1, 1944, discusses the preparation of dicarboxylic acids and their salts. In Bundesrepublik Deutschland Pat. No. 965,697, issued June 13, 1957, to Blaser and Stein, the reaction of unsaturated alcohols and their derivatives with metal carbonyls and carbon monoxide is discussed. A by-product which is obtained through the technology of Blaser et al. includes substantial amounts of monoformylated product. Similarly a formylation technique, which results in a monoformylated product when using unsaturated alcohols, is discussed in an article by Ucciani et al. in the Bull. Soc.

Chim. (France) 1969, pp. 2826-2830. Similarly, Bundesrepublik Pat. No. 1,054,444, published Apr. 9, 1959, to Waldmann and Stein, discusses the treatment of unsaturated fatty substances with formaldehyde in the presence of a carboxylic anhydride and an acidic catalyst to provide formyl products.

Substantial work has been done on the production of various hydroformylated products by the U.S. Department of Agriculture at both the Eastern and Western Regional Research Laboratories. For example, in an article by Roe entitled "Branched Carboxylic Acids from Long-Chain Unsaturated Compounds and Carbon Monoxide at Atmospheric Pressure," published at J. Am. Oil Chemists' Soc. 37, pp. 661-668 (1960), the production by direct carboxylation at atmospheric pressure of unsaturated acids with carbon monoxide or formic acid is discussed. The hydroformylation of unsaturated fatty esters is discussed by Frankel et al. at J. Am. Oil Chemists' Soc. 46, pp. 133-138 (1968). Frankel has also reported a selective catalyst system for the hydroformylation of methyl oleate utilizing rhodium catalyst in the presence of triphenylphosphine in an article entitled "Methyl 9(10)-Formylstearate by Selective Hydroformylation of Oleic Oils" at J. Am. Oil Chemists' Soc. 48, pp. 248-253 (1971).

In a paper presented at the American Oil Chemists' Society meeting in Atlantic City, N.J. in 1971, Dufek et al., discusses the esterification and transesterification of dicarboxylic acids under the title "Esterification and Transesterification of 9(10)-Carboxystearic Acid and Its Methyl Esters." The foregoing article was published at J. Am. Oil Chemists' Soc. 49 (5), pp. 302-306 (1972). Frankel, again, discusses the use of specific catalysts to obtain hydroformylated products in an article titled "Selective Hydroformylation of Polyunsaturated Fats With a Rhodium-Triphenylphosphine Catalyst," J. Am. Oil Chemists' Soc. 49, pp. 10-14 (1972). Friedrich at Vol. 17, No. 3 of Ind. Eng. Chem. Prod. Res. Dev. (1978) presents an article entitled "Low-Pressure Hydroformylation of Methyl-Oleate With an Activated Rhodium Catalyst."

Pryde, working with Frankel and Cowan discuss hydroformylation via the oxo reaction, Koch carboxylation and Reppe carbonylation in an article entitled "Reactions of Carbon Monoxide with Unsaturated Fatty Acids and Derivatives: a Review," reported at J. Am. Oil Chemists' Soc. 49, pp. 451-456 (1972).

Friedrich discusses the hydroformylation of unsaturated esters combined with catalyst recovery in an article entitled "Hydroformylation of Methyl Oleate with a Recycled Rhodium Catalyst and Estimated Costs for a Batch Process" at J. Am. Oil Chemists' Soc. 50, pp. 455-458 (1973). A similar area of technology is also reported by Frankel et al., in an article entitled "Hydroformylation of Methyl Linoleate and Linolenate with Rhodium-Triphenylphoshine Catalyst" from I&EC Product Research & Development, Vol. 12, pp. 47-53 (1973).

Certain condensation polymers prepared from pentaerythritol acetal derivatives are reported in an article "Poly(Amide-Acetals) and Poly(Ester-Acetals) from Polyol Acetals of Methyl 9(10)- Formylstearate: Preparation and Physical Characterization" reported at J. Am. Oil Chemists' Soc. 53, pp. 20-26 (1976). Compounds obtained through hydroformylation technology useful as plasticizers are discussed in a Frankel et al. article entitled "Acyl Esters from Oxo-Derived Hydroxymethylstearates as Plasticizers for Polyvinyl Chloride" printed in the J. Am. Oil Chemists' Soc. 52, pp. 498-504 (1975).

Friedrich, in an article entitled "Oxidation of Methyl Formylstearate with Molecular Oxygen" at J. Am. Oil Chemists' Soc. 53, pp. 125-129 (1976) reports the use of air or oxygen to form methyl carboxystearate from methyl formylstearate in an emulsion with a soluble rhodium complex. The reuse of catalyst in hydroformylation reactions is described by Awl in an article entitled "Hydroformylation with Recycled Rhodium Catalyst and One-Step Esterification-Acetalation: A Process for Methyl 9(10)-Methoxymethylenestearate from Oleic Acid," which is printed in J. Am. Oil Chemists' Soc. 53, pp. 190-195 (1976).

Useful diols for resin purposes are described in U.S. Pat. No. 2,933,477, issued Apr. 19, 1960 to Hostettler. Nonadecanediols are described as being utilized in urethane formulations in U.S. Pat. No. 3,243,414 to DeWitt et al., issued Mar. 29, 1966. The production of triols which are not particularly useful in resins due to the close positioning of the hydroxyl groups is reported in "Improved Synthesis of 1,1,1-trimethylolalkanes from Hexanal and Nonanal," J. Am. Oil Chemists' Soc. 45, p. 517 (July 1968) by Moore and Pryde.

Frankel et al., in a paper entitled "Catalytic Hydroformylation and Hydrocarboxylation of Unsaturated Fatty Compounds" at J. Am. Oil Chemists' Soc. 54, p. 873A (1977) also describes formylation technology. Frankel also describes the use of carbonyl metallic compounds in hydroformylations in an article entitled "Catalytic Hydroformylation of Unsaturated Fatty Derivatives with Cobalt Carbonyl" at J. Am. Oil Chemists' Soc. 53, pp. 138-141 (1976). The use of esters of various carboxystearic acids is discussed by Dufek et al. in an article entitled "Some Esters of Mono-, Di-, and Tricarboxystearic Acid as Plasticizers: Preparation and Evaluation" at J. Am. Oil Chemists' Soc. 53, pp. 198-203 (1976). Dufek et al. also report catalyst recovery in an article entitled "Recovery of Solubilized Rhodium from Hydroformylated Vegetable Oils and Their Methyl Esters" in J. Am. Oil Chemists' Soc. 54, pp. 276-278 (1977).

Frankel discusses hydroformylation generally in an article entitled "Selective Hydroformylation of Unsaturated Fatty Acid Esters" at Annals N.Y. Academy of Sciences 214:79 (1973). Catalyst technology is reviewed at "Recent Developments in Hydroformylation Catalysis" in Catal. Rev. 6 (1) page 49 et seq. (1972).

Dufek alone, at J. Am. Oil Chemists' Soc. 55, pp. 337-339 (1978) reports on the conversion of methyl 9(10) formylstearate in an article entitled "Conversion of Methyl 9(10)-Formylstearate to Carboxymethylstearate."

Acetal esters obtainable through hydroformylation technology are reported by Adlof et al. in an article entitled "Preparation and Selective Hydrolysis of Acetal Esters" at J. Am. Oil Chemists' Soc. 54, pp. 414-416 (1977). Selective catalyst systems are again reported by Frankel in the J. Am. Oil Chemists' Soc. 54, pp. 873a-881a (1977) in an article entitled "Catalytic Hydroformylation and Hydrocarboxylation of Unsaturated Fatty Compounds."

The plasticization of polyvinylchloride resins is also reported in patent applications and coded P.C. 6333 and 6375 bearing respectively the titles "Acetoxymethyl Derivatives of Polyunsaturated Fatty Triglycerides as Primary Plasticizers for Polyvinylchloride," and "Alkyl 9,9(10,10)-Bis(acyloxymethyl) octadecanoates as Primary Plasticizers for Polyvinylchloride."

Each of the foregoing, to the extent that it is applicable to the present invention, is herein incorporated by reference.

In U.S. application Ser. No. 26,854, filed Apr. 4, 1979, there are described and claimed some polyol derivatives based upon the above-described gem-bis(hydroxymethyl) alcohol compounds and poly(oxy)alkylene or caprolactone adducts and sulfates of such derivatives. Ethylene oxide adduct derivatives, propylene oxide adduct derivatives, propylene oxide capped with ethylene oxide adducts, sulfate adducts, urethane adduct derivatives and caprolactone adduct derivatives are specifically described and claimed therein.

The whole of the disclosure of those prior applications is incorporated herein by reference thereto.

OBJECTS OF THE INVENTION

An object of this invention is to provide certain new polyester polyols based upon the gem-bis(hydroxymethyl) alcohols referred to above.

Another object of this invention is to provide certain new polymeric polyols based on bis(hydroxymethyl)octadecanol with polybasic acids to make polyester polyols which have low acid numbers and which polyester polyols are useful for a variety of known polyol applications as well as for making new urethane polymers which are advantageously useful in coatings, elastomers, adhesives, and caulking and sealing compositions or formulations.

Another object of the invention is to provide a new polyester polyol based upon bis(hydroxymethyl)octadecanol, a polybasic acid and a dicarboxylic acid ester.

Another object of this invention is to provide new polyurethane polymers which are reaction products of a polyisocyanate and a new polyester polyol described herein, in either foamed or non-foamed condition, whether or not such polyurethane product contains other known ingredients, such as foaming agents, flame retardant agents, and the like.

Other objects, advantages, and purposes of this invention will become apparent from reading the specification and claims which follow.

SUMMARY OF THE INVENTION

Briefly, this invention provides certain new polymeric polyols which are the reaction products of my above-referred to gem-bis(hydroxymethyl)alkanols and polybasic acids, preferably dibasic acids, e.g., adipic acid or maleic acid, fumaric acid, or other economical di- or poly- basic acid. The reaction product can also be the result of the reaction of the new gem-bis(hydroxymethyl) alkanols, referred to hereinabove, with a dibasic or polybasic acid and a dibasic acid mono- or diester, to effect transesterification in situ to form new polyester polyol products of this invention. These new polyester polyols provide the basis for the formation of new and advantageous polyurethane products which are known to have a variety of uses, e.g., in coating compositions, polyurethane foam insulating and packaging applications, adhesives, in caulking and sealing compositions, and in applications where non-foamed hard rubber-like uses are required, giving improved wear and tear resistance.

DETAILED DESCRIPTION OF THE INVENTION

The polyester polyol products of this invention can be prepared by mixing and reacting an above-referred to gem-bis(hydroxymethyl)alkanol, preferably bis(hydroxymethyl)octadecanol, with a polybasic acid, preferably a dibasic acid such as adipic acid, or other alkane or alkene-dicarboxylic acid, in an economical, non-toxic, organic solvent which will dissolve the reactants and form an azeotrope with water by-product of the poly-esterification reaction, and heating the mixture at a temperature sufficient to drive the esterification to completion in a reasonable period of time, in the presence of an economical acid to catalyze the esterification. Sulfuric acid is a preferred catalyst. Heating of the reaction mixture to from about 100° C. to about 200° C. for from about 10 hours to about 24 hours while removing water, and returning the azeotroping liquid to the reaction mixture, is generally sufficient. Examples of azeotroping liquids include benzene, xylene, mesitylene, hexane, heptane, halogenated hydrocarbons such as dichloroethane, and the like. It is preferred to use xylene for reasons of cost and safety to employees operating the process. The molar ratio of triol to dibasic acid should not be less than about 1:1, otherwise the product will gell due to excess crosslinking if the aci number is reduced to a low value. The ratio of triol to dibasic acid should not be higher than that required to give a hydroxy equivalent weight of about 200 when the acid number is about 1.

The gem-bis(hydroxymethyl)alkanol starting materials and how to make them are described and exemplified in my above-identified prior applications. The polyol of that type for use herein can be referred to as a bis(hydroxymethyl)akanol which has the structural formula

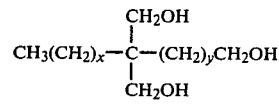

wherein the sum of x plus y ranges from 13 to 17, and preferably x plus y averages about 15 in a particular bis(hydroxymethyl)alkanol. A $C_{20}$ triol of this type is the general aim for production and use, but it is understood that in normal plant scale operation and use, the composition of the triol can be a mixture of such bis(hydroxymethyl)alkanol molecules where the sum of x plus y will vary from batch to batch and, in fact, be an average of the x and y moieties in the various molecules in the mixture. Preferably, the sum of x and y is about 14.5 to 15.5 in any given batch of triol starting material, and such sum is referred to herein as being "about 15."

The preferred $C_{20}$ triol alcohols used to make the polyester polyols of the invention can be prepared by known hydroformylation and reduction procedures referred to in my prior above-identified patent applications by converting commercially available methyl oleate to oleyl alcohol and converting oleyl alcohol to formyl octadecanol

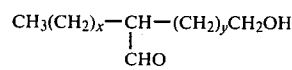

by the above-referenced hydroformylation procedure and converting the formyl octadecanol to the C$_{20}$ triol as described in application Ser. No. 081,953, filed Oct. 4, 1979 (case 4176).

Such gem-bis(hydroxymethyl) alcohols have the formula

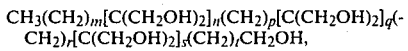
CH$_3$(CH$_2$)$_m$[C(CH$_2$OH)$_2$]$_n$(CH$_2$)$_p$[C(CH$_2$OH)$_2$]$_q$(-CH$_2$)$_r$[C(CH$_2$OH)$_2$]$_s$(CH$_2$)$_t$CH$_2$OH, wherein n plus q plus s are integers the sum of which is from 1 to 3; n, q, and s are 0 or 1; and m through t are integers, the sum of which is from 12 to 20 and t is 3 or greater.

Such gem-bis(hydroxymethyl) alcohols are formed through hydroformylation which is the process for the production of aldehydes from olefinically-unsaturated compounds by reaction with carbon monoxide and hydrogen in the presence of a catalyst. The aldehydes produced generally correspond to the compounds obtained by the addition of a hydrogen and a formyl group to an olefinically-unsaturated group in the starting material, thus saturating the olefinic bond, as referred to above.

More particularly, these gem-alcohols are prepared by hydroformylating an unsaturated alcohol of the formula

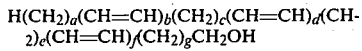
H(CH$_2$)$_a$(CH=CH)$_b$(CH$_2$)$_c$(CH=CH)$_d$(CH$_2$)$_e$(CH=CH)$_f$(CH$_2$)$_g$CH$_2$OH where, hereinafer, (1) a and g are not equal to 0; (2), the integers b plus d plus f are equal to y, which has a value of from 1 to 3; (3) the sum of the integers a plus c plus e plus g is equal to x; and (4) x plus 2y is equal to from 13 to 21; (5) m through t are integers, the sum of which is from 12 through 20; (6) n plus q plus s are 1 through 3, and; (7) n, q, and s are 0 or 1, preferably such that the sum of m through t is from 14 to 18 and x plus 2y is 15 to 19. A second preferred embodiment is where n, p, r and s are 0 and m plus t is 11 through 19. It is also preferred that n and s are 0 and q is 1.

Preferably, herein, m and t are each 4, 5 or 6, and greater. Most preferably, the starting raw material is oleyl alcohol, although linoleyl or linolenyl alcohol may be employed. It is, of course, noted that any number of synthetic unsaturated alcohols and alcohol mixtures may also be employed in the present invention. However, for the most purposes, the naturally-occurring alcohols derived from plant sources are presently most convenient and inexpensive.

The unsaturated alcohol is reacted with hydrogen gas and carbon monoxide in the presence of a rhodium catalyst, as later described, to form the corresponding formyl alcohol having the formula

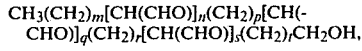
CH$_3$(CH$_2$)$_m$[CH(CHO)]$_n$(CH$_2$)$_p$[CH(-CHO)]$_q$(CH$_2$)$_r$[CH(CHO)]$_s$(CH$_2$)$_t$CH$_2$OH, wherein the various subscript numbers are as previously described.

The addition of hydrogen and carbon monoxide is accomplished in practice by conveniently adding stoichiometric amounts of the hydrogen and carbon monoxide to give the formyl alcohol. To assure completeness of the reaction, the amounts of hydrogen and carbon monoxide may be each maintained at from about 1.5:0.5 to about 0.5:1.5 molar ratio to one another. It is noted that the ratio is not critical as long as the pressure is maintained in the reaction vessel by the component gases and that the amount of hydrogen is not so great as to substantially reduce the unsaturated starting material.

The rhodium catalyst, as later described, is necessary in the hydroformylation reaction in that it has been found that the use of the more conventional cobalt catalyst results in a substantial amount of cross-linking and gelation. It is believed that the gelation is due to the coproduction of polyhemiacetals and polyacetals in competition with the production of the hydroformylated alcohol. It was first believed that it would be necessary, even with a rhodium catalyst, to employ the ester of the unsaturated alcohol, e.g., oleyl acetate, to avoid the unwanted by-products. Of course, the ester is more expensive and eventually is converted to the alcohol in any event.

Higher yields of product are obtained through the use of the rhodium catalysts than if a cobalt catalyst is employed. It has also been observed that a much higher degree of isomerization of the double bond occurs with a cobalt catalyst than with a rhodium catalyst.

The conditions for pressure and temperature during the batch hydroformylation are conveniently conducted at from about 90 degrees C. to about 170 degrees C., preferably from about 100 degrees C. to about 130 degrees C. Above the higher temperatures listed above, increased amounts of unwanted by-products are formed in the reaction mixture. The pressure conditions are such that the pressure in the scaled system is maintained at from about 20 to about 500 atmospheres, preferably from about 30 to about 100 atmospheres absolute, during the hydroformylation. Higher temperatures and pressures are employed when using a continuous process.

The preferred end product obtained from conducting the foregoing process is 9(10) formyl octadecanol when the starting material is oleyl alcohol. The positioning of the 9(10) indicates that the product obtained is a mixture of the 9 and 10 isomer with respect to the formyl group. One additional reason for using a rhodium catalyst is that, if a cobalt catalyst were employed, a considerable amount of terminal aldehyde would be formed due to bond migration prior to the addition of the formyl group. When the terminal aldehyde group is formed, the resultant alcohol, obtained by carrying out the remainder of the herein-described process, is unsuitable for many of the purposes that the geminal alcohols may be utilized for.

It should also be appreciated that, if 9,12-linoleyl alcohol is the starting material, then the formyl alcohol so formed will be a 9(10), 12(13) diformyloctadecanol. That is, the end product obtained here will actually be a mixture of the 9-12, 9-13, 10-12, 10-13 diformyl alcohols. Similarily, without discussing all the particular isomers present when 9,12,15-linolenyl alcohol is employed, the product so obtained will be a mixture of the 9(10), 12(13), 15(16) triformyloctadecanol isomers.

It is particularly important that the expensive rhodium catalyst is recovered. This may be conveniently done by distillation of the formyl alcohol leaving the rhodium in the residue. What is particularly surprising is that the rhodium can be recovered from the distillate, in that the art would predict that, when hydroformylating an unsaturated alcohol, the products obtained would include considerable quantities of polyhemiacetals and polyacetals as a portion or all of the reaction product, and that these products would not be recoverable by distillation. Thus, not only is the desired end product achieved in a high degree of purity and yield through the use of the rhodium catalyst, but the rhodium catalyst is recoverable in extremely high quantities from the reaction mixture.

It may be stated that the polyacetal and polyhemiacetal formation might be prevented by the utilization of the corresponding unsaturated acid or its ester in place of the unsaturated alcohol. However, this substitution, which eventually involves the acid ester, is undesirble in that an aqueous neutralization step is required, which forms a soap as a by-product. The soap so formed then emulsifies the reaction products and the water present to make separation extremely difficult, thus diminishing recovery of both the alcohol and the expensive catalyst. Thus, the present invention is highly selective to both the unsaturated alcohol and the particular rhodium catalyst so employed.

Any convenient source of rhodium may be employed, as in the present reaction mixture; the rhodium catalyst is actually converted through the presence of the hydrogen and carbon monoxide into its active form, which is a rhodium carbonyl hydride. Conveniently, the source of rhodium for use in the rhodium catalyst may be rhodium chloride, rhodium dicarbonyl chloride dimer, rhodium nitrate, rhodium trichlorite and other similar materials.

The rhodium catalyst in the present hydroformylation reaction is preferably present with a ligand, such as trisubstituted phosphine or trisubstituted phosphite. The term trisubstituted includes both alkyl and aryl compounds and the substituted compounds of the alkyl and aryl compounds. A particularly valuable ligand for the rhodium carbonyl hydride is triphenylphosphite or triphenylphosphine in that both compounds are particularly useful in minimizing migration of the double bond, thereby avoiding a large number of isomers with respect to the formyl group, including the undesired terminal formyl compound, as previously discussed. In general, triarylphosphines or triarylphosphites may be used for this purpose in the formation of the rhodium carbonyl hydride ligand. In addition, the foregoing materials are extremely valuable in minimizing the undesired reaction of saturation of the double bond or the reduction of the formyl group,. This frequently occurs in the absence of such ligands because the rhodium catalyst functions excellently as a hydrogenation catalyst. That is, the ligand tends to eliminate such side reactions.

In general, any one of several other additional ligands may be used with the rhodium catalyst. Such additional ligands are discussed in the "Selective Hydroformylation of Unsaturated Fatty Acid Esters" by Frankel in the Annals N.Y. Academy of Sciences 214:79 (1973).

The various ligands are conveniently employed in mole ratio to the rhodium metal content of the catalyst of from about 2 to 50, preferably from about 3 to 20. The rhodium catalyst, based upon its metal content, is conveniently employed in catalytic amounts, preferably from about 20 ppm to about 10,000 ppm, most preferably from about 50 ppm to about 500 ppm by weight of the unsaturated alcohol.

The various formyl alcohols are useful, as previously stated, in preparing the highly desired gem-bis(hydroxymethyl) alcohols. The alcohols may be formed from the foregoing formyl alcohols via a Tollens' reaction (aldol) condensation followed by a crossed-Cannizzaro reaction).

Schematically, the Tollens' reaction is as described below:

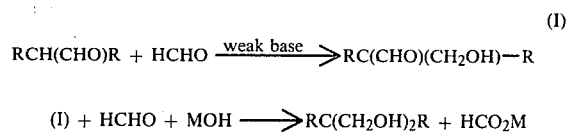

$$(I) + HCHO + MOH \longrightarrow RC(CH_2OH)_2R + HCO_2M$$

wherein in the above formula R indicates an organic moiety, compound (I) is a hydroxymethyl aldehyde and MOH is a strong base.

The Tollens' reaction is thus carried out by reacting one mole of a monoformylated alcohol with two moles of formaldehyde in an inert atmosphere such as nitrogen. Where the formyl alcohol contains more than one formyl group, two moles of formaldehyde are required for each formyl group present. Thus, if the reactant is formyloctadecanol, then two moles of formaldehyde are required for conversion to the gem-bis (hydroxymethyl) alcohol whereas, if linoleyl alcohol is utilized in the first instance to give a diformyloctadecanol, then four moles of formaldehyde are required to obtain the di-gem-bis(hydroxymethyl)octadecanol. Conveniently, an excess of up to 1.5, preferably up to 1.2, times the amount of formaldehyde actually required to form the corresponding gem-bis(hydroxymethyl) alcohol is employed. A convenient manner of adding the formaldehyde in the Tollens' reaction is by using a methanol solution of formaldehyde.

The Tollens' reaction utilizes a strong base as both a reactant and a catalyst. Such strong bases include sodium, potassium or calcium hydroxide. Other strong bases, such as carbonates or other hydroxides, may be used as well. The strong base is conveniently employed on an equivalent basis per formyl group to convert the formyl group to the hydroxy methyl group. The amount of base required in the Tollens' reaction is at least an equivalent of that required, preferably up to 1.5, most preferably up to 1.2 equivalents. The Tollens' reaction is conducted at a temperature of from about 0 degrees C. to about 100 degrees C., preferably from about 20 degrees C. to about 70 degrees C.

The crude gem-bis (hydroxymethyl) alcohol so formed is washed with water to remove any excess caustic and salts formed and then obtained in a relatively pure state by vacuum drying.

In obtaining the gem-bis (hydroxymethyl) alcohol, the crossed-Cannizzaro reaction predominates over the rate of reaction for the simple Cannizzaro reaction. The Cannizzaro reaction, which is promoted by base, water, and heat, is the process by which an aldehyde reacts with itself to form the corresponding alcohol and formate salt. That is, the formyl group on the formyl alcohol reacts faster with formaldehyde to give the alcohol than does the formaldehyde react with itself.

It is also surprising that the formation of hemiacetal, which may be acid or base, catalyzed, does not occur upon the addition of base to the formyl alcohol while forming the intermediate hydroxymethyl formyl alcohol. Thus, two potential side reactions, the Cannizzaro and the hemiacetal formation (and thereafter the acetal) which might be expected, given the reactants and the processing conditions involved, do not in fact occur, and the useful alcohol is obtained in substantial quantities.

It has been found, however, that the more complicated crossed-Cannizzaro surprisingly predominates in rate and amount of product [gem-bis(hydroxymethyl) alcohol] produced despite the steric hindrance of the larger formyl alcohol molecule even under conditions which are known to promote the simple Cannizzaro reaction.

An alternative method of accomplishing the formation of the gem-bis(hydroxymethyl) alcohol is to use only about one-half the equivalent amount of the formaldehyde required in the Tollens' reaction, thereby forming the corresponding hydroxymethyl formyl alcohol via the aldol condensation. That is, the hydroxymethyl group is attached to the carbon in the alpha position to the formyl group. Where a polyformyl alcohol is the intermediate product, the formaldehyde is halved from that utilized in the Tollens' reaction to give the corresponding polyhydroxymethyl polyformyl alcohol.

This variation of forming the gem-bis (hydroxymethyl) alcohol eliminates the need for the strong base required in the Tollens' reaction and utilizes instead only catalytic amounts of base which may be either a weak or strong base. A preferred weak base is triethylamine. Even here, some care must be taken, as it is possible even when using a weak base to obtain compound (I), as the Cannizzaro reaction may compete with the aldol condensation.

The hydroxymethyl formyl alcohol so formed by this alternative route is then reduced to the alcohol conveniently, by using hydrogen gas and a suitable hydrogenation catalyst, such as copper, or nickel, via conventional hydrogenation practice, or by lithium aluminum hydride reduction. A significant advantage to the alternative route is the absence of large amounts of salt and solvents needed in the Tollens' reaction route.

A distinct advantage in the gem-bis(hydroxymethyl) alcohol is that it is a ligant at room temperature and, further, has no tertiary hydrogens which are a weak point for chemical attack on the molecule.

The polybasic acid reactant has from 4 to about 36 carbon atoms per molecule and is preferably a $C_4$ to $C_{10}$-dicarboxylic acid, examples of which are well known in the chemical literature. Examples include maleic acid, fumaric acid, 1,5-pentanedicarboxylic acid, adipic acid, 1,7-heptanedicarboxylic acid, sebacic acid, 1,10-decanedicarboxylic acid, heptadecanedicarboxylic acids (such as described in U.S. Pat. Nos. 3,864,314 and 2,891,084) and $C_{21}$ or $C_{22}$ dicarboxylic acids (such as described in U.S. Pat. Nos. 3,821,075 and 3,899,476), and dicarboxylic acids having single or double carbon-to-carbon unsaturation or additional hydroxy groups therein, such as itaconic acid, itamalic acid, and malic acid. Other useful dicarboxylic acids are the well-known dimeric dicarboxylic acids resulting from the polymerization of unsaturated fatty acids. The dicarboxylic products resulting from the dimerization of the $C_{18}$ unsaturated fatty acids such as oleic, linoleic, or linolenic will contain 36 carbon atoms. These acids and their corresponding alcohols or glycols are generally discussed in U.S. Pat. No. 3,511,792, including references to other patents relating thereto.

Aromatic dicarboxylic acid esters which may optionally be incorporated into the reaction mixture include the o-, m-, and p-phthallic acid $C_1$ to $C_2$ esters, e.g., the dimethyl and diethyl esters of phthallic, isophthallic and terephthallic acids, and the exters of trimellitic acid and similar tri-carboxylic acids, when some degree of three-dimensional polymerization my be desired later in use applications of the polyol.

As indicated above, one aspect of this invention involves the use of these new polyester polyols as the polyol component in making new polyurethane products by reaction of the new polyol with a polyisocyanate by known procedures and in known formulations for making foamed or non-foamed polyurethane products. Suitable polyisocyanates and other components of the polymeric reaction mixture are exemplified in prior application Ser. No. 26,854, filed Apr. 4, 1979. For example, suitable polyisocyanates include ethylene diisocyanate, trimethylene diisocynate, hexamethylene diisocyanate, propylene-1,2-diisocyanate, ethylidene diisocyanate, cyclopentylene-1,3-diisocyanate, the 1,2-, 1,3-, and 1,4-cyclohexylene diisocyanates, the 1,3- and 1,4-phenylene diisocyanates, polymethylene polyphenylene-isocyanates, the 2,4- and 2,6-toluene diisocyanates, the 1,3- and 1,4-xylylene diisocyanates, bis (4-isocyanatophenyl)methane, 4,4'-diphenyl-propane diisocyanates, bis(2-isocyanatoethyl) carbonate, 1,8-diisocyanato-p-methane, 1-methyl-2,4-diisocyanatocyclohexane, the chlorophenylene diisocynates, naphthalene-1,5-diisocyanate, triphenylmethane-4,4',4''-triisocyanate, isopropylbenzene-alpha-4-diisocyanate,5,6-bicyclo[2.2.1]hept-2-ene diisocyanate, 5,6-diisocyanatobutylbicyclo[2.2.1]hept-2-ene, and similar polyisocyanates.

Of particular interest in the present invention are trimethylene hexamethyl diisocyanate available from VEBA, and heptadecyl (C17) diisocyanate, DDI® 1410, an aliphatic C-36 diisocyanate available from the Henkel Corporation of Minneapolis, Minn. (Generally, diisocyanates having from 12 to 40 carbons in the aliphatic radical may be used in the present invention, e.g., toluene diisocyanate, available from Allied Chemical; isophorone diisocyanate, available from VEBA; and Desmodur N, an aliphatic triisocyanate, available from Mobay). Desmodur N is more particularly defined as the tri-isocyanate adduct of 3 moles of hexamethylene diisocyanate and water having an isocyanate equivalent weight, as later defined, of 191 grams. Other adducts or prepolymers of polyisocyanates include Desmodur L and Mondur CB, which are the adduct of toluene diisocyanate. The foregoing materials have an isocyanate equivalent weight of approximately 250 grams.

The amount of the polyisocyanate utilized in forming the urethane compositions of this invention is expressed on a percentage equivalent weight basis with respect to the hydroxyl functionality of the alcohol. Desirably, each hydroxyl functional group on the alcohol will react on a 1:1 stoichiometric basis with the isocyanate functionality on the polyisocyanate compound. It is quite feasible, however, to form the urethane linkage using from about 80 percent to 120 percent, preferably from about 95 percent to 105 percent, on a hydroxyl-isocyanate equivalent basis, of the polyisocyanate to form the urethane product.

To determine the amount of the polyisocyanate required for a given saturated polyol, the hydroxyl or isocyanate equivalent weight of the respective polyol or polyisocyanate is determined as that weight in grams of the material which contains one gram equivalent weight of the respective functional group. More particularly, to determine the number of equivalents in a given saturated polyol, the hydroxyl value is first determined by known methods and reported in milligrams of potassium hydroxide. The calculation to determine the hydroxyl equivalents is then given by the following equation:

$$\text{OH equivalent weight} = \frac{56{,}100}{\text{OH value}},$$

where 56,100 is the milligram equivalent weight of potassium hydroxide.

Alternatively, if the weight percentage of the hydroxyl groups in the saturated polyol is known, the hydroxyl equivalent is determined as follows:

$$\text{OH equivalent weight} = \frac{17 \times 100}{\text{wt \% OH}},$$

where 17 is the equivalent weight of the hydroxyl radical and the weight percent OH is the percentage of the saturated polyol which is hydroxyl groups.

In similar fashion, the isocyanate equivalent may be determined if the weight percent of the isocyanate functional groups in the polyisocyanate is known. This equation is given below, where 42 is the molecular weight of an isocyanate functional group and the weight percent NCO is that portion of polyisocyanate made up of isocyanate functional groups:

$$\text{isocyanate equivalent weight} = \frac{42 \times 100}{\text{wt \% NCO}}.$$

To form the urethane reaction product, the polyester polyol of the present invention and the organic polyisocyanate are merely mixed together in the proper proportions. When utilized as a coating, the compounds are then quickly spread with a knife blade, brushed, or sprayed over the surface of the article to be coated. Where molded articles are desired, various techniques, such as injection molding, are employed. Specific technique for forming urethane reaction products is hereinafter described in the examples.

If desired, various urethane catalysts may be employed to promote the reaction. Examples of such urethane catalysts include triethylene diamine, morpholine, N-ethyl-morpholine, dimethyl piperazine, triethylamine, N,N,N',N'-tetramethylbutane-1,3-diamine, dibutyltin dilaurate, stannous octoate, stannous laurate, dioctyltin diacetate, lead octoate, stannous oleate, stannous tallate, dibutyltin oxide, and hexabutylditin, as well as other art-recognized urethane catalysts. Typical levels of the urethane catalyst are from about 0.001 percent to about 5 percent by weight of the urethane linking components.

An additional polyol may be included with the alcohols of the present invention. Such polyols may be an alkyl or cycloalkyl polyol, an ether-linked polyol, an ether and ester-linked polyol, or hydroxy functional acrylic copolymers.

Specific examples of alkyl and cycloalkyl polyols include 2,5-hexanediol available from Aldrich Chemical; 1,6-hexanediol, available from Celanese Chemical; ethylene glycol available from Baker; Dimerol or dimer glycol, a 36 carbon diol prepared from the dimerized fatty acids discussed earlier herein; which dimer glycols are discussed in U.S. Pat. Nos. 2,347,562, 2,413,612, and 3,091,600, among other references; glycerol, 1,2,6-hexanetriol available from Union Carbide; pentaerythritol, and 1,4-cyclohexane diol. Additional examples of such polyols include Poly BD R-45HT ™, a butadiene diol having an approximate molecular weight of 2800, available from Arco; and, trimethylol propane available from Celanese Chemical.

The ester-linked saturated diols of the present invention are more particularly described as polyols where the predominate linkage (functional group other than the hydroxyl) are ester radicals. The ester-linked saturated polyols are structurally represented as

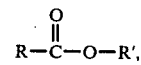

where R and R' are organic residues which contain at least two hydroxyl radicals and at least one ester link.

Examples of ester-linked saturated polyols include Niax PC00200 ™ and PCP0240 ™, both available from Union Carbide and having respective molecular weights of approximately 530 and 2000. Both of the foregoing compounds are diols. Niax PCP0300, also available from Union Carbide, is a caprolactone-ester triol having approximate molecular weight of 540. Niax PCP0310 ™, also available from Union Carbide, is a caprolactone-ester triol having a molecular weight of approximately 900.

The ether-linked saturated polyols of the present invention include compounds such as diethylene glycol and triethylene glycol, both available from Fisher. Further ether-linked saturated polyols useful in the present invention include the Polymeg Q0650 ™, Q0100 ™, and Q0200 ™, all of which are ether diols available from Quaker, having a respective molecular weight of approximately 650, 1000, and 2000. Pluracol P1010 ™, having an approximate molecular weight of 1050, available from Wyandotte, is an example of a polypropylene oxide ether-linked diol useful in the present invention. Similar Wyandotte products useful as saturated polyols in the present invention include Pluracol TP440 ™, and 150, which are propylene oxide ether-linked triols having respective molecular weights of approximately 425 and 1560. In similar fashion, Pluracol GP3030 ™ is another saturated polyol suitable for the present invention, available from Wyandotte. The foregoing material is a glycerine polypropylene ether-linked triol having an approximate molecular weight of 2900.

Additional Pluracols ™ useful in the present invention include Pluracol PEP450, which is a pentaerythritol polypropylene oxide ether-linked tetrol, having a molecular weight of 405, and Pluracol 493, an ether-linked tetrol having a molecular weight of approximately 3630.

Ester and ether-linked saturated polyols suitable in the present invention are described structurally as

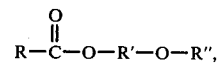

where R, R', and R" are organic residues containing at least two hydroxyl radicals and at least one ester and one ether linkage.

Detailed examples of how to prepare the polyester polyols of this invention are set forth hereinbelow without any intent that these examples be limiting as to the scope of the invention. Throughout the specification and claims hereof, the percentages and ratios are by weight and the temperatures are in degrees Celsius, unless otherwise indicated.

EXAMPLE I

A polyester polyol is prepared by reacting 131.2 grams (1.8 equivalents) of adipic acid with 414 grams (3.6 equivalents) of bis(hydroxymethyl)octadecanol in 100 grams of xylene which serves as the azeotrope to remove water of condensation. The reaction is maintained at 175° C. for a period of twenty hours, 0.13 grams of concentrated sulfuric acid being added at the beginning and 0.05 grams later on in the reaction. The water removed is collected in a Dean and Stark tube. At the end of the heating period, the xylene is removed under vacuum leaving a viscous liquid which at 22.5° C. has a viscosity of 175 PA/S, Pascal-seconds (sometimes also designated as Pa·s or merely Pas), an acid value of 0.9, and a hydroxy equivalent weight of 356. In U.S. Pat. No. 4,045,389, the reference to "Pas" is made with 1 Pas equal to 10 poises. In a subsequent patent to the same inventors, U.S. Pat. No. 4,150,002, the term is "Pa·s."

This polyester polyol (50.6 grams, 0.142 equivalents) and 125.3 grams (0.833 equivalents) of hydroxymethyl octadecanol are blended at room temperature. To this is added 88.6 grams (1.0 equivalent) of toluene diisocyanate with stirring under vacuum. After three minutes the temperature rises spontaneously to 55° C. and the reaction product thereafter is poured into metal molds. The elastomer is cured 22.5 hours at 100° C. The polymer sets to a solid before one hour of the final cure time has passed.

This elastomer is evaluated for hardness, strength, water absorption, hydrolytic stability, and resistance to torsional stress at low temperatures. The findings follow:

| | |
|---|---|
| Hardness, Shore Durometer, D Scale (ASTM-D-2240-75) | 66 |
| Tensile strength at break, PSI (ASTM-D-412-75) | 3630 |
| Tensile strength at yield, PSI (ASTM-D-412-75) | 1380 |
| Elongation at break, % (ASTM-D-412-75) | 160 |
| Compression Set, % (ASTM-D-395-69) | 22.5 |
| Water absorption, 24 hrs, 70° C., grams/1000 cc | 8.6 |
| Hydrolytic stability, retention of tensile strength after 18 hrs, wet steam 125° C. (14 PSI), % | 71 |
| $T_f$, temperature to achieve 45,000 modulus, °C. (ASTM-D-1043-72) | −7 |

EXAMPLE II

A second polyester polyol is produced by reacting 414 grams (3.6 equivalents) of bis(hydroxymethyl)octadecanol with 43.74 grams (0.6 equivalents) of adipic acid and 58.26 grams (0.6 equivalents) of dimethyl isophthalate in 150 grams of xylene as azeotrope using as catalyst 1.81 grams of dibutyl tin oxide. Over a period of about four hours the temperature is raised to 180° C. by gradual removal of xylene by distillation. The temperature is then maintained at 180° C. for about 6½ hours, after which no further water evolves and the xylene is removed by distillation under vacuum. The polyester polyol has a viscosity of 43.8 PA/S, an acid number of 0.1, and a hydroxy equivalent weight of 202.

EXAMPLE III

To 170 grams of toluene containing 3.49 grams of dibutyl tin oxide catalyst were added 673.4 grams (1.952 moles) of bis(hydroxymethyl)octadecanol and 325 grams (0.975 moles) of heptadecane dicarboxylic acid, (a $C_{19}$ diacid). The reactants were heated and stirred with a nitrogen atmosphere, gradually distilling off toluene and water through a Dean and Stark take-off unit. Over a period of 7½ hours the temperature was raised from an initial 153° C. to 190° C. while taking off water. The next day the heating was continued for 6 hours at 190° C. until the acid value of 0.7 based on solids was obtained.

The product was stripped of the remaining toluene on a rotary evaporator. The product analyzed as follows:
Acid No.=0.7
Hydroxyl equivalent weight=278
Visc. at 23° C.=132.4 poises

EXAMPLE IV

To 150 grams of toluene containing 1.76 grams of dibutyl tin oxide catalyst were added 276 grams (0.8 mole) of bis(hydroxymethyl) octadecanol and 228 grams (0.4 mole) of VERSADYME ®52, a polymerized tall oil fatty acid having the following analysis:
Saponification value—196.8
Saponification Equivalent weight—285.1
Acid Value—195.4
% Monomer (M)—2.3
% Intermediate (I)—3.5
% Dimer (D)—91.0
% Trimer (T)—3.2

The temperature was raised from an initial 128° C. to 185° C. in 2½ hours and maintained there for 11 hours using the same procedure and apparatus as in Example III above. The product was stripped and analyzed as follows:
Acid No.=0.3
Hydroxyl equivalent weight=328.5
Visc. at 23° C.=415 poises It is to be understood that the invention is not to be limited to the exact details of operation or structure shown and described, as obvious modifications and equivalents will be apparent to one skilled in the art.

What is claimed is:

1. A polyester polyol which is the reaction product of
(a) a gem-polyol of the formula $CH_3(CH_2)_m[C(CH_2OH)_2]_n(CH_2)_p[C(CH_2OH)_2]_q(CH_2)_r[C(CH_2OH)_2]_s(CH_2)_t CH_2OH$, wherein n, q, and s are separate numbers totaling 1 to 3; each of n, q, and s is 0 or 1; the sum of m through t totals 12 to 20; and t is 3 or greater; and,
(b) an alkane- or alkene- di- or tri-carboxylic acid having 4 to 10 carbon atoms, inclusive, condensed to the extent so as to have an acid number below about 10, a viscosity of at least 40 PA/S units, and a hydroxy equivalent weight of at least about 200.

2. A polyester polyol according to claim 1, wherein the polyol reactant is a triol of the formula $$CH_3(CH_2)_x-\underset{\underset{CH_2OH}{|}}{\overset{\overset{CH_2OH}{|}}{C}}-(CH_2)_y CH_2OH$$

wherein x plus y equals a sum between about 13 and 17.

3. A polyester polyol according to claim 2, wherein the sum of x plus y is about 15.

4. A polyester polyol according to claim 1, wherein the acid reactant is a $C_4$ to $C_{10}$-alkane dicarboxylic acid.

5. A polyester polyol according to claim 4, wherein the $C_4$ to $C_{10}$-alkane dicarboxylic acid is adipic acid.

6. A polyester polyol according to claim 1, which further includes as a reactant therein a $C_1$ or $C_2$-alkyl ester of a phthalic acid.

7. A polyester polyol according to claim 6, wherein the phthallic acid ester reactant is methyl isophthallate.

* * * * *

UNITED STATES PATENT AND TRADEMARK OFFICE
CERTIFICATE OF CORRECTION

PATENT NO. : 4,307,224
DATED : December 22, 1981
INVENTOR(S) : Edgar R. Rogier

It is certified that error appears in the above—identified patent and that said Letters Patent is hereby corrected as shown below:

Col. 1, line 30; the formula is hyphenated incorrectly and should be hyphenated with the "(" on the second line, reading -- $(CH_2)$ --
Col. 1, line 33; delete "plus"  Response and Amendment dated May 15, 1981, page 1.
Col. 3, line 56; "Triphenylphoshine" should read -- Triphenylphosphine --
Col. 6, line 28; "gell" should read -- gel --
Col. 6, line 28; "aci" should read -- acid --
Col. 6, line 37; "bis(hydroxymethyl)akanol" should read -- bis(hydroxymethyl)alkanol --
Col. 7, line 8; the formula is hyphenated incorrectly and should be hyphenated with the "(" on the second line, reading -- $(CH_2)$ --
Col. 7, line 27; the formula is hyphenated incorrectly and should be hyphenated with the "$)_e$" on the first line, reading -- $(CH_2)_e-$ --
Col. 7, line 31; "hereinafer" should read -- hereinafter --
Col. 7, line 55; the formula is hyphenated incorrectly and should be hyphenated with the "(" on the second line, reading -- $(CHO)]_q$ --
Col. 9, line 9; "undesirble" should read -- undesirable --
Col. 9, line 25; "trichlorite" should read -- trichloride --
Col. 11, line 38; "ligant" should read -- liquid --
Col. 11, line 41; "4to" should read -- 4 to --
Col. 11, line 65; "p-phthallic" should read -- p-phthalic --

UNITED STATES PATENT AND TRADEMARK OFFICE
CERTIFICATE OF CORRECTION

PATENT NO. : 4,307,224
DATED : December 22, 1981
INVENTOR(S) : Edgar R. Rogier

It is certified that error appears in the above—identified patent and that said Letters Patent is hereby corrected as shown below:

Col. 11, line 66; "phthallic" should read -- phthalic --
Col. 11, line 66; "isophthallic" should read -- isophthalic --
Col. 11, line 67; "terephthallic" should read -- terephthalic --
Col. 11, line 67; "exters" should read -- esters --
Col. 12, line 13; "diisocynate" should read -- diisocyanate --
Col. 12, line 23; "diisocynates" should read -- diisocyanates --
Col. 12, line 44; "adduct" should read -- adducts --
Col. 16, line 38; the formula is hyphenated incorrectly and should be hyphenated with the "(" on the second line, reading -- $(CH_2)$ --
Col. 16, line 67; "phthallic" should read -- phthalic --
Col. 16, line 67; "isophthallate" should read -- isophthalate --

Signed and Sealed this

Twentieth Day of September 1983

[SEAL]

Attest:

GERALD J. MOSSINGHOFF

Attesting Officer

Commissioner of Patents and Trademarks